United States Patent [19]

Kopp et al.

[11] Patent Number: 4,696,187

[45] Date of Patent: Sep. 29, 1987

[54] CHROMATOGRAPHY METHOD

[75] Inventors: Reiner H. Kopp, Copake; Allen I. Panetz, Huntington, both of N.Y.

[73] Assignee: Biochemical Diagnostics, Inc., Farmingdale, N.Y.

[21] Appl. No.: 696,399

[22] Filed: Jan. 30, 1985

Related U.S. Application Data

[60] Division of Ser. No. 410,490, Aug. 23, 1982, which is a continuation of Ser. No. 232,134, Feb. 6, 1981, Pat. No. 4,351,800.

[51] Int. Cl.⁴ .......................................... G01N 31/08
[52] U.S. Cl. ............................... 73/61.1 C; 436/162; 422/70; 210/198.3
[58] Field of Search ................... 73/61.1 C; 436/161, 436/162; 422/70, 100, 90; 210/198.3

[56] References Cited

U.S. PATENT DOCUMENTS

| | | | |
|---|---|---|---|
| 3,189,413 | 6/1965 | Davis | 422/70 |
| 3,523,890 | 8/1970 | Stahl | 210/198.3 |
| 3,738,493 | 6/1973 | Cummins et al. | 210/198.3 |
| 3,766,884 | 10/1973 | Rosenthal | 422/70 |
| 3,833,341 | 9/1974 | Tocci | 422/70 |
| 3,843,051 | 10/1974 | Thoden | 422/70 |
| 3,988,921 | 11/1976 | Lightner | 73/61.1 C |
| 4,004,548 | 1/1977 | Smola et al. | 422/70 |
| 4,134,730 | 1/1979 | Quame | 436/162 |
| 4,272,381 | 6/1981 | Kramer et al. | 422/70 |
| 4,283,199 | 8/1981 | Szabo | 422/70 |
| 4,309,286 | 1/1982 | Lenihan, Jr. et al. | 73/61.1 C |
| 4,351,800 | 9/1982 | Kopp et al. | 422/70 |

Primary Examiner—Stewart J. Levy
Assistant Examiner—Hezron E. Williams
Attorney, Agent, or Firm—Hoffmann, Dilworth, Barrese & Baron

[57] ABSTRACT

A method for rapidly transferring chromatography or adsorption column eluates in a continuous flow directly to the chromatography plate for continuous evaporation of the solvents at a rate compatible with the flow.

2 Claims, 5 Drawing Figures

CHROMATOGRAPHY METHOD

RELATED APPLICATIONS

This applicational is a divisional of application Ser. No. 06/410,490, filed Aug. 23, 1982, entitled Chromatography Apparatus and Method, now pending, which application is a continuation of application Ser. No. 06/232,134, filed Feb. 6, 1981, now U.S. Pat. No. 4,351,800.

BACKGROUND OF THE INVENTION

Thin layer chromatography, referred to in laboratory parlance as TLC, has become an increasingly useful tool for detecting tiny amounts of drugs in specimens. The analysis procedure involves the extraction of drugs from biological fluids by passing the specimen or drug-containing fluid through a chromatography or adsorption column containing a packing medium. The drugs are eluted from the column by an appropriate organic solvent which is then evaporated, to concentrate the drugs. In a second procedure the concentrated residue is redissolved in a few drops of solvent which is transferred as a spot onto the chromatography plate. THe deposition is dried, and thereafter the plate is activated with solvent to initiate the detectable migration patterns on the plate surface thus revealing the identity of the compounds or drugs contained in the specimen. In this fashion urine samples are screened for barbituates, opiates, amphetamines and other narcotics. Equipment and techniques heretofore available have made the screening of multiple samples both expensive and time-consuming.

The present invention has for its object to provide a new design for an applicator and an application and column assembly which will allow the direct application of the column eluate to a chromatography plate with the eluate drying in a small spot as it reaches the plate surface.

SUMMARY OF THE INVENTION

In accordance with the invention an applicator for spotting dissolved compounds for analysis on chromatography plates can include an imperforate sheath having a metering wick or core of porous material in its lower end and projecting out of the sheath in a point. Above the core the sheath forms a liquid solvent reservoir as well as a receptor for a chromatography eluting column which can be detachably coupled to the applicator after a specimen has previously been passed through its adsorbing or absorbing packing to entrain drugs or compounds for analysis by thin layer chromatography. The assembly is mounted in a supporting and processing unit for holding the assembly in engagement with the chromatography plate and in which heat and moving air are directed over the point of engagement to evaporate the solvent as fast as it flows through the metering core onto the plate. The solvent is poured into a reservoir at the top of the column so that elution occurs in the packing as the solvent moves downward, carrying the dissolved drug or chemical to the metering core and then, at a controlled flow rate, to the chromatography plate for concentration.

THE PREFERRED EMBODIMENT

Figure 1:
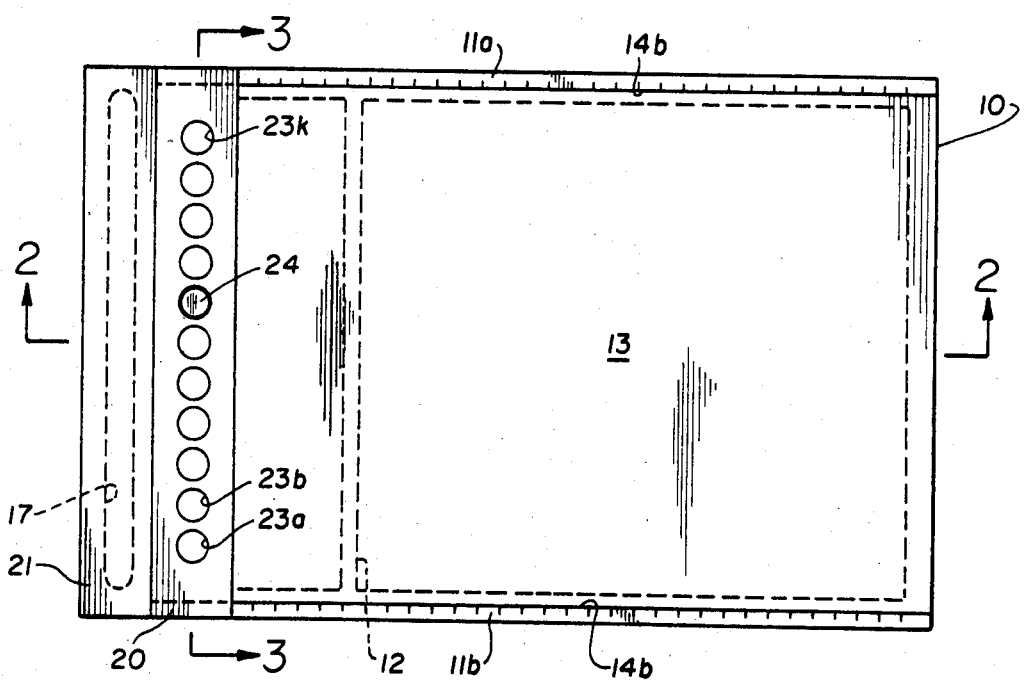
FIG. 1 is a top view of a thin layer chromatography plate supporting and processing apparatus formed in accordance with the present invention.
Figure 2:
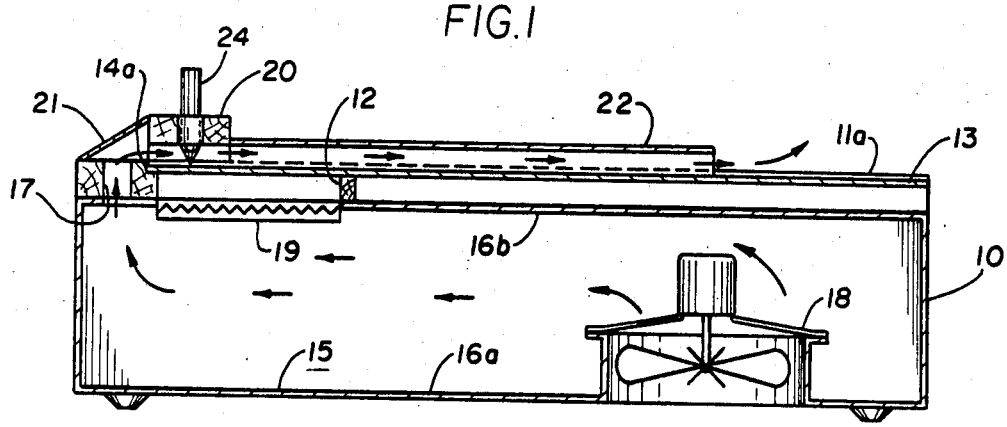
FIG. 2 is a view in vertical longitudinal section taken on line 2—2 of FIG. 1 looking in the direction of the arrows.
Figure 3:
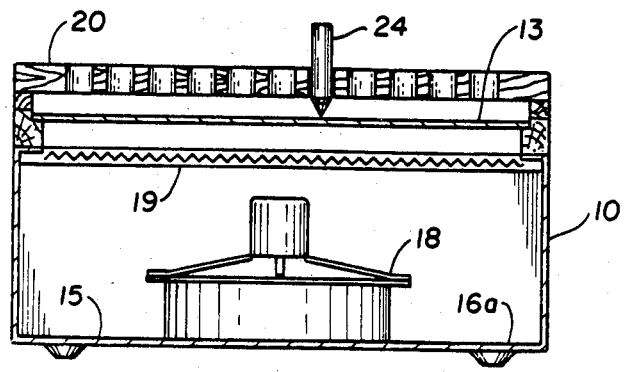
FIG. 3 is a view in vertical transverse section taken on line 3—3 of FIG. 1 looking in the direction of the arrows.

Referring to FIGS. 1-3, there is shown a thin layer chromatography (TLC) plate supporting and processing apparatus comprising a housing 10 having calibrated side rails 11a and 11b extending longitudinally, and a transverse rail 12 which together constitute the supports for a TLC plate 13. The plate 13 is accurately positioned within the housing by means of stops 14a and 14b near the forward end of the unit and disposed in the plane of mounting of the plate.

The hollow body of the housing defines an internal chamber 15 bounded by a bottom 16a vented to the atmosphere and a top 16b. The chamber 15 is placed in communication with the TLC plate 13 by means of an air slot 17 formed at one end of the top 16b. A fan assembly 18 draws ambient air into the housing through the vented bottom where it is warmed by an electrical resistance heating pad 19 secured to the under surface of the top 16b at a point close to the air slot 17 and precisely beneath the area of the TLC plate where spotting occurs, all as described below.

The transverse sample applicator holder 20 is supported near the end of the housing adjacent the air slot 17, with the air being directed from the slot into the horizontal space between the underside of the applicator holder 20 and the upper surface of the TLC plate by a baffle plate 21. If desired, the horizontal flow path between the TLC plate can be increased in length by a removable lid 22 abutting the edge of the applicator holder. The applicator holder 20 is formed with an array of holes 23a, 23b . . . 23k adapted to receive sample applicators 24 which are adapted to engage the surface of the TLC plate to deposit or "spot" specimens thereon for chromatographical analyses. The apparatus described briefly above is disclosed and claimed in the applicants' application Ser. No. 06/232,134, now U.S. Pat. No. 4,351,800.

Figure 4:
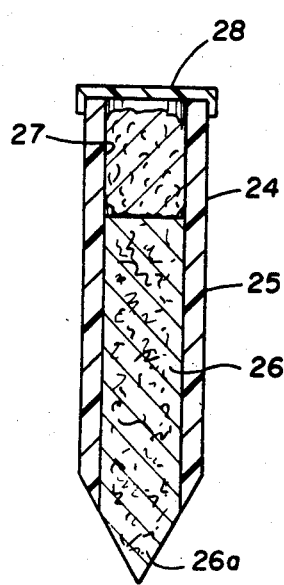
FIG. 4 is a view of vertical section in enlarged scale of a spotting applicator for use in the apparatus of FIGS. 1-3.

Referring to FIG. 4, the applicator 24 (shown in enlarged scale) includes an imperforate cylindrical sheath 25 preferably formed of plastic, such as polyethylene or polypropylene, into which is fitted a wick or metering core 26 of porous material which in the embodiment of FIG. 4 can take the form of porous polyethylene having a pore size of 5 to 10 microns. The tip 26a is sharpened to define a point. The tip is preferably designed to deposit a small spot of solvent and specimen on the plate 13, typically 0.5 to 1.0 cm. in diameter. The sheath 25 extends beyond the inner end of the core to define a solvent reservoir 27 which can be sealed by a removable cap 28. If desired, the reservoir can include a packed cotton wad to control the flow of liquid solvent through the core.

To carry out an analysis, the sample is first dissolved in a volatile organic solvent. The sample is picked up by the applicator by immersing the exposed tip into the dissolved sample. It is important at this stage that the solvent bearing the sample not spread through the entire length of the core 26 but that the absorption terminate before the material spreads into the cotton pack in the solvent reservoir 27. After removal from the sample source, the sample applicator 24 is then placed in one of the mounting holes 23a . . . 23k of the applicator holder 20 to position the pointed tip of the applicator on the surface of the TLC plate 13 in a precisely defined position. An aliquot of organic solvent, typically 20 to 400 microliters, is pipetted into the reservoir which can then be covered or left open as desired. The packed cotton slowly releases the solvent in the reservoir, allowing it to travel downward through the porous core 26 carrying the sample with it onto the TLC plate. Alternatively, the dissolved sample can be placed directly on the cotton pack in the solvent reservoir 27, this being followed by an aliquot of organic solvent in a manner described above. The sample is deposited in a small spot, typically 0.5 to 1.0 cm. in diameter. The exact spot size is determined by the TLC plate temperature, which is controlled by the electrical resistor heating pad 19 mounted close to the under side of the plate, the forced airflow volume derived from the fan 18 and passed through the air slot 17 to flow over the TLC plate in the narrow channel defined by the baffle 21 and the under side of the transverse applicator holder 20, and the volatility of the solvent.

With the spot size and position now defined and the specimen to be analyzed free of its initial solvent vehicle, the TLC plate with its array of sample spots can be removed from its support and the lower edge dipped into a chromatography solvent in accordance with standard procedures, after which the specimens with their unknown compound contents migrate upwardly along the plate surface. After a predetermined time interval, the plate can be removed from the chromatography solvent and returned to the supporting apparatus where the calibrations in the side rails 11a and 11b will indicate how far up the plate the unknown material solvent traveled. The apparatus can also be used to drive off the TLC solvents from the plate, to heat it via the heating pad 19 or to cool it by means of the air currents, all as might be required for chemical reactions to occur on the plate surface. It will be understood that the lid or cover 22 is not used for later stages of the process.

While the invention has been described having reference to preferred embodiments, it will be understood that it can take various other forms and arrangements within the scope of the invention. For example, the core of the sample applicator can constitute a paper wick or porous medium containing ion exchangers to selectively hold back compounds from elution. Also, immobilized antibodies, enzymes or other reactant compounds may be incorporated into the porous media as an aid in gaining more sample selectivity.

Figure 5:
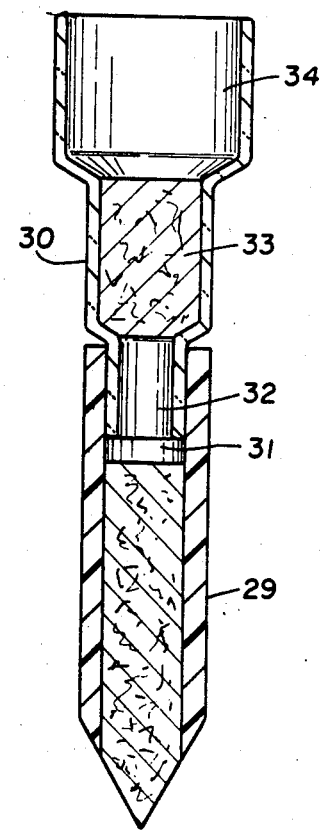
FIG. 5 is a view in vertical section of a spotting applicator assembly utilizing portions of the spotting applicator of FIG. 4.

As shown in FIG. 5, an applicator 29 of generally similar configuration to that shown in FIG. 4 is used with a charged chromatography column 30 inserted in the upper space 31 corresponding to the reservoir 27 of the spotting applicator 24 of FIG. 4. The column 30 includes in addition to its depending discharge end 32 seated in the space 31, a sample holding chamber containing column packing material 33 which can as is well known in the art be selected from a variety of materials including absorbers, adsorbers, special resins, such as Amberlite, XAD-2, or the like, surmounted by a combination specimen and solvent reservoir 34. The column 30 and applicator 29 are normally assembled only after the column has first been exposed to a throughput of the liquid specimen such as urine to be analyzed for drugs or other chemicals. The specimen gravitates through the column packing allowing the latter to take up as by absorption or adsorption possible compounds such as drugs in the specimen which are to be later identified in the thin layer chromatography process. The waste liquid material not entrained in the packing is discharged to a waste source through the discharge 32. The chromatography column is then ready for the elution step which precedes chromatography.

In accordance with the present invention, the column as charged and ready for elution is assembled with the applicator as shown in FIG. 5 and the two are placed in the spotting and processing apparatus of FIGS. 1-3. A solvent for one or more of the compounds under analysis is then poured into the reservoir 34 where is percolates through the packing medium 33 to dissolve the compounds after which it gravitates to the clean metering wick or core 26. The charged solvent is then metered on to the thin layer chromatography plate 13 at a predetermined rate which is selected at a value such that the solvent is evaporated from the plate 13 before it can exceed a spot size of say 0.5 to 1.0 centimeters in diameter, all as described above. The evaporation rate is controlled by the combination of heating from the resistance heater 19 and ducted air flow through the air slot 17 across the surface of the plate 13 and around the depending wick tip 26a of the applicator. In this fashion the steps of elution and spotting are carried out as a single continuous operation. The ensuing procedure for chromatography analysis by observing migration patterns is conventional and well known in the art.

We claim:

1. In a method of eluting and spotting for identifying unknown substances by chromatography beginning with a column in which the packing medium has the unknown substance entrained therein, the steps of placing the spotting applicator on the chromatography plate in contact therewith to establish a point of spotting;

establishing a continuous flow path from the column to the chromatography plate;

placing an eluting solvent into the column above the packing medium;

metering the flow directly to the plate while causing air to blow over the plate at the point of spotting, thereby to establish a continuous solvent flow from the column above the packing media through the applicator to the plate and controlling the spot size and concentrating the unknown substance by the evaporation due to the flow of air.

2. The method as set forth in claim 1, including the step of heating the air and evaporating the solvent by controlling the heat and flow of the air over the plate around the spotting applicator to maintain a spot size in the range of 0.5 to 1.0 centimeters in diameter.

* * * * *